United States Patent [19]

Sivaramakrishnan et al.

[11] Patent Number: 5,198,428
[45] Date of Patent: Mar. 30, 1993

[54] MACROPHAGE CYTOTOXIN COMPOSITIONS AND METHODS OF PREPARATION

[75] Inventors: Mathoor Sivaramakrishnan, The Woodlands; Stanley D. Tucker, Houston; Jim Klostergaard, Kingwood; Gabriel Lopez-Berestein, Houston, all of Tex.

[73] Assignee: Board of Regents, The Univ. of TX System, Austin, Tex.

[21] Appl. No.: 681,867

[22] Filed: Apr. 5, 1991

[51] Int. Cl.⁵ .......................................... A61K 31/715
[52] U.S. Cl. .......................................... 514/54; 514/8; 424/85.1; 530/395
[58] Field of Search ................. 514/54, 8; 424/85.1; 530/395

[56] References Cited

U.S. PATENT DOCUMENTS 4,650,674  3/1987  Agarwal et al. ...................... 424/85

OTHER PUBLICATIONS

Kilbourn et al., *Dissertation Abstracts International* 45(05):1424A (Nov. 1984).
Kilbourn et al., *J. Immunol.* 133(5):2577–2581 (1984).
Kilbourn, et al., *J. of Immunol.* 144(3):1042–1045 (1990).
Albina, et al., *J. of Immunol.*, 143(11):3641–3646 (1989).
Stuehr et al., *J. Exp. Med.* 169:1543–1555 (1989).
Albina et al., *J. Exp. Med.* 169:1021–1029 (1989).
Albina et al., *Fed. Am. Soc. Exp. Biol. J.* 3(4), A966 (Mar. 1989).
Amber, et al., *J. Leuk. Biol.* 44:58–65 (1988).
Amber et al., *J. Leuk. Biol.* 43:187–192 (1988).
Klostergaard et al., *J. Immunol. Meth.* 101:97–108 (1987).
Klostergaard et al., *Cancer Research* 47:2014–2019 (1987).
Stuehr et al., *J. Immunol.* 139(2):518–525 (1987).
Hibbs, Jr., et al., *Science* 235:473–476 (1987).
Hibbs, Jr., et al., *J. Immunol.* 138(2):550–565 (1987).
Granger et al., *J. Clin. Invest.* 65:357–370 (1980).
Stewart-Tull et al., *J. Med. Microbiol.* 5:67–73 (1972).
Amber et al., *J. Leukoc. Biol.* 46:307 (1989).
Drapier and Hibbs, *J. Clin. Invest.* 78:790–797 (1986).
Granger and Lehninger, *J. Cell. Biology* 95:527–535 (1982).
Hibbs et al., *Biochem. Biophys. Res. Comm.* 123:716–723 (1984).

*Primary Examiner*—Johnnie R. Brown
*Assistant Examiner*—Pamela S. Webber
*Attorney, Agent, or Firm*—Arnold, White & Durkee

[57] ABSTRACT

This invention provides a cytotoxin composition that inhibits mitochondrial respiration and causes cytostasis in cells, independent of nitric oxide. The invention comprises a conditioned supernatant derived from macrophage cell line (EA13.5) that inhibits mitochondrial respiration and causes cytostasis in cells. More particularly, the invention comprises a macrophage cytotoxin obtained from conditioned supernatant collected from cultured EA13.5 cell. This macrophage cytotoxin (1) inhibits mitochondrial respiration, (2) causes cytostasis independent of L-arginine derived nitric oxide, (3) is a weakly acidic (pI of about 7.5 to 8.0) glycoprotein (as determined by binding to lentil lectin sepharose). The invention also discloses a method for producing an L-arginine-derived nitric oxide-independent macrophage cytotoxin by culturing EA13.5 cells, adding IFN-γ and lipopolysaccharide to trigger secretion of the macrophage cytotoxin into the conditioned supernatant, collecting the conditioned supernatant, and isolating the macrophage cytotoxin from the conditioned supernatant. Further disclosed by this invention is a method for producing a nitric oxide independent macrophage cytotoxin, that inhibits mitochondrial respiration independent of L-arginine, from cultured rodent macrophages.

6 Claims, 5 Drawing Sheets

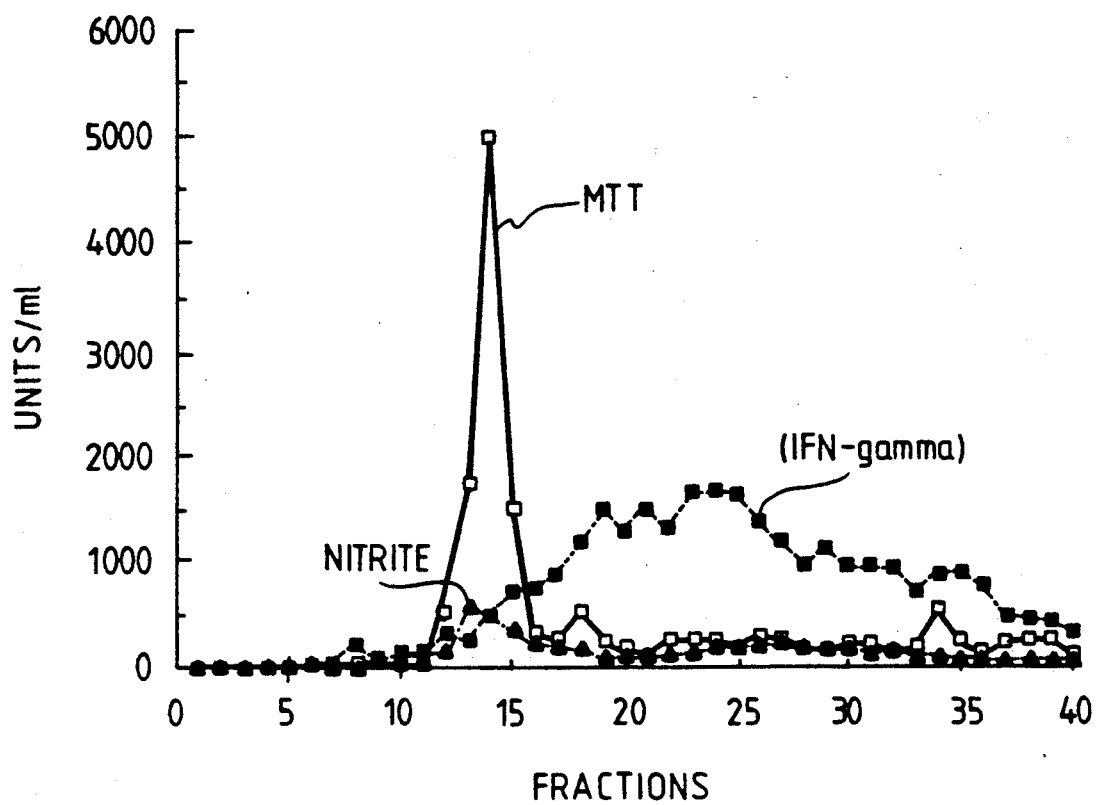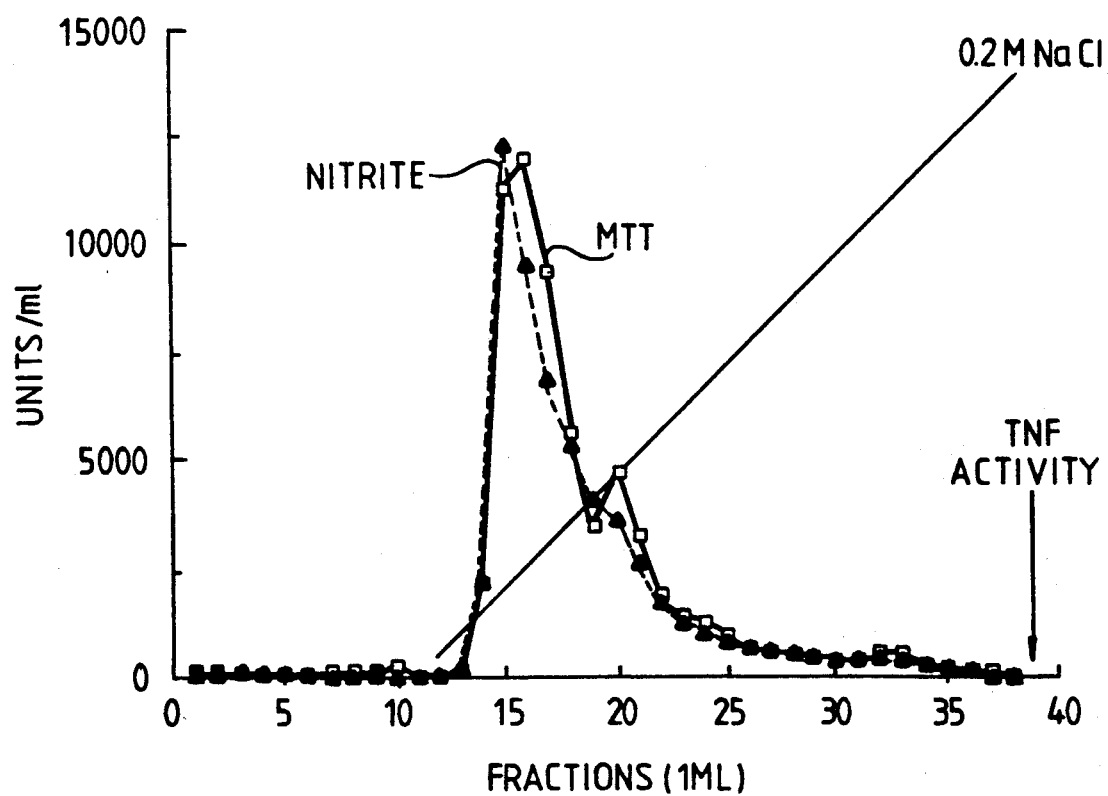

MACROPHAGE CYTOTOXIN COMPOSITIONS AND METHODS OF PREPARATION

BACKGROUND OF THE INVENTION

1. Field of the Invention

This invention relates to a cytotoxic agent directed against tumor cells. In particular, the invention is directed to a cytotoxin derived from a macrophage cell line.

2. Description of Related Art

Activated macrophages become cytotoxic to tumor cells in response to various biological and microbial signals. Inhibition of mitochondrial respiration, loss of intracellular iron, and loss of aconitase activity by L-arginine-dependent pathways, have been shown to result from macrophage cytotoxic activity against tumor cells.

Recent studies suggest that one mechanism of macrophage-mediated cytotoxicity is L-arginine dependent via the oxidative degradation of L-arginine to nitric oxide (NO). Thus, NO has been proposed to be a chemically reactive component that leads to tumor cell mitochondrial respiration inhibition, loss of intracellular iron, inhibition of aconitase activity, and inhibition of DNA synthesis. NO is probably an active intermediate as established by the following criteria: (a) macrophages, upon activation, release nitrite and nitrate (NO) in an L-arginine-dependent manner; (b) the production of NO by macrophages has been directly demonstrated; and (c) NO alone has been shown to mimic some cytotoxic effects attributed to activated macrophages. [Hibbs et al., L-Arginine is Required for the Expression of the Activated Macrophage Effector Mechanism Causing Selective Metabolic Inhibition of Target Cells, J. Immunol. 138:550-565 (1987) and Stuehr et al., Nitric Oxide: A Macrophage Product Responsible for Cytostasis and Respiration Inhibition in Tumor Target Cells, J. Exp. Med., 169:1543-1545 (1989)].

Studies from our laboratory as well as others (Amber et al., J. Leukoc. Biol. 43; 187-192 (1988) and Amber et al., J. Leukoc. Biol. 44:58-65 (1988)) have shown that the L-arginine-dependent nitric oxide effector mechanism, is probably mediated by a combination of interferon-gamma with TNF, IL1 or LPS present in the conditioned supernatants. This conclusion was derived from the following observations. 1) significant amounts of nitric oxide were produced in EMT-6 cells upon treatment with macrophage conditioned supernatants and 2) the mitochondrial respiration inhibition was directly proportional to the amount of L-arginine (from which nitric oxide is derived) present in the culture medium and 3) the respiration inhibition and nitrite production were probably caused by a combination if IFN-γ and TNF present in the conditioned supernatants since the bioactivity was almost completely neutralized by anti-interferon-γ (78%) and anti-TNF antisera (11%), shown by in vitro experiments (Amber, et al, J. Leukoc. Biol. 46:307 (1989)).

One study has stated that L-arginine deficient environments enhance resident macrophage metabolism, functions, and viability (Albina et al., An L-Arginine (ARG) Deficient Environment Enhances Resident Macrophage Metabolism, Functions and Viability, Fed. Am. Soc. Exp. Biol. J., 3(4), A966 (March 1989)). This study involved measuring increased macrophage viability and therefore did not focus on the cytotoxicity contained in the supernatant collected from the cultured macrophages.

Another reference disclosed experiments which employed conditioned supernatant collected from activated murine peritoneal macrophages. The authors demonstrated that conditioned supernatant, obtained from activated macrophages, contained a component that inhibited tumor cell mitochondrial respiration. Mitochondrial respiration was measured by EMT-6 cell's ability to oxidize succinate, malate, and tetramethylphenylenediamine (Kilbourn et al., Activated Macrophages Secrete A Soluble Factor That Inhibits Mitochondrial Respiration of Tumor Cells, J. Immunol., 133:2577-2581 (1984); Kilbourn, R. G., Inhibition of the Mitochondrial Respiration of Tumor Cells by Soluble Factors Released by Activated Macrophages, A Ph.D. Dissertation presented to the Faculty of The University of Texas Health Science Center at Houston Graduate School of Biomedical Sciences [May, 1984], Dissertation Abstracts International, 45(5):1424B-1425B, November, 1984). Kilbourn et al (1984) also reported that the conditioned supernatant inhibited DNA synthesis in EMT-6 cells (used to measure the level of cytostasis induced in the target cells). Fractionation of conditioned supernatant by molecular exclusion resulted in the recovery of two peaks that both demonstrated respiration inhibition activity. The authors demonstrated that these two peaks, eluting at 55,000 and 80,000 daltons, mediated the inhibition of malate and succinate oxidation and were cytostatic for EMT-6 cells. The peritoneal macrophage conditioned supernatant described by Kilbourn et al. (1984) are obtained under conditions very similar to that described by Amber et al. (Amber et al., J. Leukoc. Biol. 43:187-192 (1988)) and therefore the observed mitochondrial respiration inhibition is very likely to be mediated via the nitric oxide pathway by IFN-γ and potentially by a combination of other cytokines.

The present invention provides a cytokine that acts via a different mechanism than earlier described macrophage cytotoxin.

This present invention therefore discloses a method for producing a cytokine that causes cytostasis and mitochondrial respiration inhibition independent of nitrite production. This cytokine is obtained by culturing an independently established macrophage cell line (EA13.5), adding IFN-γ and lipopolysaccharide to trigger the secretion of the macrophage cytotoxin into the media, allowing its isolation.

SUMMARY OF THE INVENTION

The present invention provides a cell free composition of a macrophage cytotoxin that (1) inhibits mitochondrial respiration, causes cytostasis, all independent of nitric oxide, IFN-γ, as well as TNF (determined by MTT assay, Nitrite assay, ELISA for IFN-γ, neutralred assay); (2) is a weakly acidic protein (determined by binding to DEAE-5PW and IEF); (3) is a glycoprotein (determined by binding to lentil-lectin sepharose); and (4) has a molecular size between 40,000 daltons and 50,000 daltons (determined by gel filtration).

The present invention also provides a method of inhibiting mitochondrial respiration and causing cytostasis in a tumor cell derived from mammals by contacting the cell with the macrophage free cytotoxin composition, in an amount effective to inhibit mitochondrial respiration and cause cytostasis in the cell.

This invention further embodies a method to produce a macrophage cytotoxin involving: a) culturing EA13.5 cells in EXCELL 300 medium; b) adding IFN-γ (in a concentration ranging from 1 u/ml to 100 u/ml) and lipopolysaccharide (in a concentration ranging from 1.25 nanomolar to 125 nanomolar) to trigger secretion of a macrophage cytotoxin into supernatant; c) separating the supernatant from the cultured macrophages; and d) collecting the supernatant containing said macrophage cytotoxin, wherein said macrophage cytotoxin: i) is a weakly acidic (pI of about 7.5-8.0) glycoprotein (as determined by binding to lentil lectin); ii) inhibits mitochondrial respiration; and iii) causes cytostasis.

A sample of EA13.5 cells was deposited with the American Type Culture Collection on Nov. 20, 1991, and was assigned Accession Number CRL 10934.

This instant invention provides a method of producing a cytokine that causes mitochondrial respiration inhibition and causes cytostasis by culturing macrophages or macrophage cell lines; establishing macrophage cell lines that can be induced to release increased quantities of this cytokine; triggering the cell line EA13.5 by treatment with IFN-γ and LPS; producing the cytokine in conditioned media that may contain between 0.01%-5% fetal calf serum, between 0-6 μg/ml of transferrin, and between 0-5 μg/ml of insulin; isolating the nitric oxide independent cytokine.

This invention discloses a cytotoxin composition that inhibits mitochondrial respiration and induces cytostasis in tumor cells derived from mammals. The invention comprises a conditioned supernatant derived from EA13.5 cells cultured in media containing low protein levels. This conditioned supernatant inhibits mitochondrial respiration and causes cytostasis in tumor cells derived from mammals. More particularly, the invention comprises a cell-free composition obtained as conditioned supernatant collected from cultured macrophages effective for inhibiting mitochondrial respiration in a cell.

For the purpose of this invention, cytostasis refers to a process whereby cells stop growing and eventually die. Conditioned supernatant is defined as the culture medium in which cells have been triggered for cytotoxin release which therefore contains proteins secreted by the triggered cells.

For the purpose of this invention, any macrophages or cell lines established from any macrophages will suffice, however, the inventors prefer to employ EA13.5 macrophage cell line, as well as murine macrophages. For the purpose of this invention, the target cells that the macrophage cytotoxin will kill are mammalian cells, and, the inventors prefer human and rodent, in particular. For the purpose of this invention, cytokine and cytotoxin are interchangeable.

For the purpose of this invention, the macrophage cytotoxin is isolated from conditioned supernatant obtained from EA13.5 cells in EX-CELL 300 medium. It is possible to obtain the macrophage cytotoxin by triggering murine peritoneal macrophages under restricted conditions and using specialized media conditions. A comparison of some of the characteristics of this cytotoxin isolated from EA13.5 to its counterpart isolated from peritoneal macrophage conditioned supernatants are described below. Further for the purpose of this invention, the source of the rodent macrophages is either rat or mouse.

The invention can be used to treat an animal with cancer by administering the macrophage cytotoxin composition of this invention to the animal in an effective amount for inhibiting mitochondrial respiration of the tumor cells, wherein the amount is sufficient to suppress tumor cell growth and eventually lead to tumor cell death. Enhanced production of this nitric oxide independent macrophage cytotoxin may be used in the treatment of diseases such as cancer, infections, and other inflammatory processes.

BRIEF DESCRIPTION OF THE DRAWINGS

FIG. 1. Signals required for activation and triggering nitric oxide independent production of macrophage cytotoxin by EA13.5 cells.

FIG. 3A demonstrates the dose-dependent effect of lipopolysaccharide (o) on the inhibition of mitochondrial respiration mediated by rIFN-γ (with IFN-γ at a concentration of 100 units/ml), as well as the dose responsive inhibition of mitochondrial respiration with rIFN-γ (■; with LPS at a concentration of 25 nanomolar). Specific methods are set forth in Example II.

FIG. 3B demonstrates the dose-dependent inhibition of mitochondrial respiration for EMT-6 treated with conditioned supernatant (Δ). Specific methods are set forth in Example II.

FIG. 4A presents the molecular size determination by gel filtration of conditioned supernatant from EA13.5 macrophage cell line by studying both mitochondrial respiration inhibition (□), as well as nitrite production (Δ). Specific methods for obtaining cell-line conditioned supernatant are set forth in Example I.

FIG. 4B presents the molecular size determination by gel filtration of conditioned supernatant from peritoneal macrophages by studying both mitochondrial respiration inhibition (□), as well as nitrite production (Δ). Specific methods for obtaining macrophage conditioned supernatant are set forth in Kilbourn et al., Activated Macrophages Secrete A Soluble Factor That Inhibits Mitochondrial Respiration of Tumor Cells, J. Immunol., 133:2577-2581 (1984); Kilbourn, R. G., *Inhibition of the Mitochondrial Respiration of Tumor Cells by Soluble Factors Released by Activated Macrophages*, A. Ph.D. Dissertation presented to the Faculty of The University of Texas Health Science Center at Houston Graduate School of Biomedical Sciences [May, 1984], Dissertation Abstracts International, 45(5):1424B-1425B, November, 1984.

FIG. 5A. FIG. 5A shows the effect of conditioned supernatant/DEAE-fractions on mitochondrial respiration inhibition (□), nitrite production (Δ) and the distribution of IFN-γ (■). Specific methods for obtaining 6 hr macrophage conditioned supernatant are set forth in Example II.

FIG. 5B. FIG. 5B shows the effect of conditioned supernatant DEAE-fractions on mitochondrial respiration inhibition (□), nitrite production (Δ), and tumor necrosis factor activity. Specific methods for obtaining 18 hr macrophage conditioned supernatant are set forth in Kilbourn et al. (see FIG. 4B for reference).

DESCRIPTION OF THE PREFERRED EMBODIMENTS

Figure 1A:
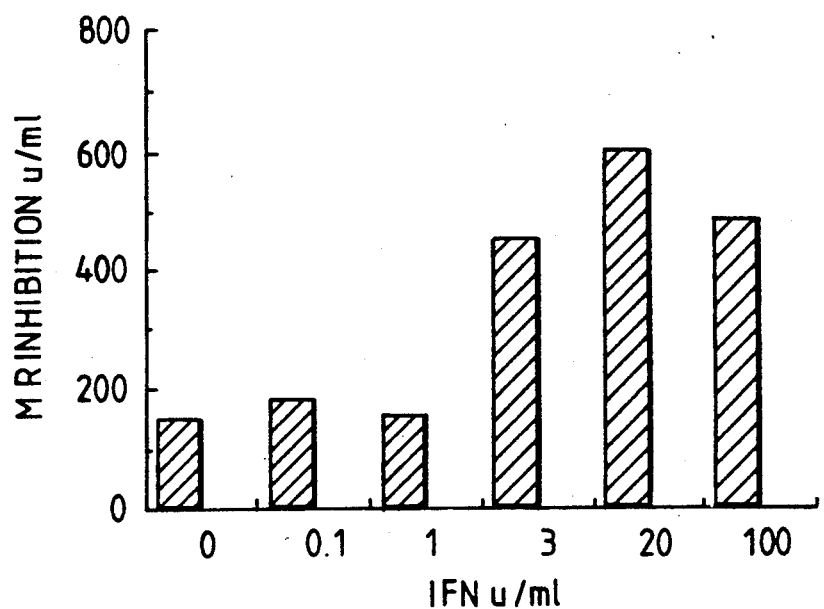
In FIG. 1A IFN-γ was added at the indicated levels to activate EA13.5 cells for 9h at which time 12.5 nanomolar of LPS was added.

The following example details the materials, methods and experimental design employed to study nitric oxide independent macrophage cytotoxin. Briefly, L-arginine independent macrophage cytotoxin is prepared by culturing macrophage cells in selected media, especially in L-arginine deficient media.

EXAMPLE I

MACROPHAGE CYTOTOXIN, DERIVED FROM A NEW CELL LINE, THAT DISPLAYS MITOCHONDRIAL RESPIRATION INHIBITION INDEPENDENT OF IFN-γ

This Example describes the selection and characterization of a clone (EA13.5) derived from the RAW 264.7 murine macrophage-like cell line. EA13.5 cells can be activated by treatment with IFN-γ and LPS to release a factor(s) that induced mitochondrial respiration inhibition in EMT-6 cells. Furthermore, this mitochondrial respiration inhibition of EMT-6 was independent of both IFN-γ and TNF.

1. MATERIALS AND METHODS EMPLOYED

A. Materials and Reagents Used

Bacterial lipopolysaccharide (*E. coli* serotype 0128:B12 phenol extracted, LPS), MTT dye, MTT formazan, neutral red dye, and cycloheximide were obtained from Sigma Chemical Co. (St. Louis, Mo.). $N^G$-monomethyl-L-arginine (NMA) was purchased from Calbiochem, San Diego, Calif. The ELISA kit for mouse interferon gamma (IFN-γ) was obtained from Amgen Biologicals (Thousand Oaks, Calif.). Endotoxin-screened fetal calf serum (FCS) and powdered DME/F12 medium were obtained from Hazelton Research Products (Lenexa, Kans.). EX-CELL 300 medium, purchased from J R Scientific (Woodland, Calif.). The media used in this study were determined to contain less than 1.25 nanomolar (1 ng/ml) LPS based on LAL test (Associates of Cape Cod, Woods Hole, Mass.). Bacillus Calmette Guérin (BCG) was a generous gift from Leric Goodman (Antigen Supply House, Chatsworth, Calif.).

B. Cell Lines and Peritoneal Macrophages Employed

The macrophage-like cell line RAW264.7 and L929 cells were obtained from the American Type Culture Collection, Rockville, Md. The murine mammary adenocarcinoma EMT-6 cell line was supplied by Dr. R. Kallman, Stanford University. EMT-6 and L929 cells were maintained in DME/F12 medium containing 5% FCS. RAW264.7 and clones of these cells were maintained in either DME/F12 medium containing 10% FCS or EX-CELL 300 medium containing 0.2% FCS.

Peritoneal macrophages were obtained in a manner described previously (Klostergaard et al., *J. of Immunol. Methods* 101:97–108 (1987)) with minor modifications: Eight- to twelve-week-old CD-1 Swiss male mice (Harlan Sprague Dawley, Inc., Indianapolis, Ind.) were injected intraperitoneally with $1 \times 10^7$ colony-forming units of BCG 24 and 4 days before Mφ were harvested by peritoneal lavage. Peritoneal exudate cells were centrifuged and resuspended in DME/F12 containing 10 mM HEPES buffer pH 7.4 and penicillin and streptomycin. Cells were allowed to adhere for 2h at a density of $1.8 \times 10^6$ cells/cm$^2$ surface area. The plates were rinsed gently three times with DME/F12 medium HEPES containing penicillin and streptomycin to remove nonadherent cells, then various media indicated (0.48ml/cm$^2$) were added to the plates. Wright-Giemsa staining revealed that the adherent cells were 85 to 90% macrophages with approximately 8 to 13% lymphocytes and 2% polymorphonuclear cells. The adherent peritoneal macrophage cultures were triggered by the addition of LPS to achieve a final medium concentration of 110 nanomolar ($10^{-9}$).

C. Production of Conditioned Supernatants From Raw264.7 and EA13.5 Cell Lines RAW264.7 and EA13.5 were maintained in either DME/F12 medium containing 5–10% FCS or in EX-CELL 300 medium containing 0.2% FCS and 10 to 25mM HEPES, pH 7.4. Media previously conditioned by growth of either RAW264.7 or EAI13.5 was added (10%) to the fresh media to provide any autologous growth factors that may be released by the cells. Both of these macrophage cell lines were able to grow adherent to tissue culture dishes to a maximum density of approximately $1 \times 10^6$ cells per ml. For purposes of producing conditioned supernatant in a low protein containing medium, the cells were grown in EX-CELL 300 containing 0.2% FCS. When the macrophage cell line reached a density of $0.5 \times 10^6$ cells per ml or higher, production of the conditioned supernatant was triggered by activation of the macrophages with IFN-γ (2 ou/ml). Following a period of 6 to 12 hours of IFN-γ treatment, the cells were triggered with LPS (12.5 nanomolar). In order to produce the conditioned supernatant in a low protein containing medium, the medium was changed by centrifugation of the cells after treatment with IFN-γ and replacement of the cells in fresh medium containing LPS. The conditioned supernatant was collected approximately 18h after triggering with LPS.

D. Assay for Mitochondrial Respiration Inhibition

The effect of conditioned supernatant on the mitochondrial respiration of EMT-6 cells was determined using the MTT assay performed as previously described. EMT-6 target cells ($8 \times 10^3/100$ μl) were cultured in DME/F12 containing 5% FCS penicillin and streptomycin in 96-well plates. Following overnight incubation, 50 μl of test samples was added in triplicates to the first row of the target plate and titered so that the successive wells corresponded to 1:3 dilutions. After a further 18h of incubation, 10 μl of 5 mg/ml MTT (Sigma Chemicals) was added to each well. Reduction of MTT to its formazan was allowed to continue for 60 min. at 37° C.; the plates were then inverted and blotted dry. MTT formazan was resolubilized by the addition of 100 μl of DMSO. Absorbance was read at 570 nm in a plate reader. The value of mitochondrial respiration (MR) inhibition, expressed in units per ml, was obtained by calculating the amount of the dilution of 1 ml of the test substance that caused 50% of the maximum inhibition of formazan production. The maximum level of formazan production (no MR inhibition) was measured for untreated control target cells and the minimum level of formazan production (maximum MR inhibition) was measured using target cells treated with undiluted conditioned supernatant.

E. Assay for Nitrite Synthesis

The induction of nitric oxide synthesis by tumor cells was determined using a colorimetric assay for nitrite as was previously described (Green et al., Anal. Biochem. 126:131-138 (1982)). To determine the nitrite concentration in the same wells used for the mitochondrial respiration inhibition assay, 50 μl of the target cell media were removed at the termination of the 18h incubation prior to MTT addition and dispensed into a secondary plate. The original plate was used in the mitochondrial respiration inhibition assay described above with the addition of 60 μl of fresh media containing MTT, to yield a final concentration of 0.5 mg/ml MTT dye. The concentration of nitrite in the media was determined on the secondary plate by adding 60 μl of Greiss reagent (1% sulfanilamide, 0.1% naphthylethylenediamine dihydrochloride, 2.5% phosphoric acid) and measuring the absorbance at 540 nm in a plate reader. The value for induction of nitrite production by EMT-6 cells, in units per ml, was obtained by calculating the amount of the dilution from 1 ml of the test sample that induced the target cells to produce 50% of the maximal amount of nitrite. The maximum amount of nitrite produced was determined by measuring EMT-6 cells treated with undiluted conditioned supernatant, while the minimum or background was determined by measuring untreated cells.

F. Production of Nitrite by Mφ

The concentration of endogenous nitrite produced by the Mφ was determined by adding an equal volume of Greiss reagent to 50 μl of test conditioned supernatant in triplicate. A standard curve for quantitating nitrite production was constructed using dilutions of a stock sodium nitrite solution.

G. Assay for TNF

TNF in conditioned supernatant was quantitated using L929 cells as targets (23). L929 cells were seeded at $1.5 \times 10^4$ per well in a 96-well flat-bottom plate and incubated overnight. Following the addition of actinomycin D (1.0 μg/ml), the test substance was added to the first row in triplicates and titered at dilutions of 1:3. After 18h of incubation, neutral red was added to each well at a final concentration of 0.002%. Following an additional 2h of incubation, the plates were washed with PBS and the bound dye was resolubilized with 70% ethanol, 0.6% glacial acetic acid. The absorbance was read at 540 nm in a plate reader. The value for TNF activity in units per ml was obtained by calculating the amount of the dilution from 1 ml that yielded 50% lysis of the L929 monolayer. The minimal cytolysis was measured for untreated targets and the maximal cytolysis was measured using targets treated with a standard preparation of conditioned supernatant.

H. Assay for Mouse IFN-γ by ELISA

The ELISA for mouse IFN-γ was performed in accordance with the instructions of the supplier, Amgen Biologicals. Basically, a standard curve consisting of IFN-γ standards at 0, 5, 10, 20, and 40 u/ml was included in each assay. Each unknown sample was diluted to 2 to 40 fold depending upon the dilution required to bring the concentration within the standard range. Using the absorbance value of the unknown, the corresponding concentration of IFN-γ was determined based on the standard curve, multiplied by the dilution factor.

I. Measurements of Oxygen Consumption

EMT-6 tumor cells were plated at $1 \times 10^6$ cells per 100 mm dish in DME/F12 media containing 5% FCS and penicillin and streptomycin and then incubated at 37°. Test supernatants were added to the plates approximately 24h later and incubated for an additional 18h. The treated cells were collected and permeabilized with digitonin as described by Klostergaard et al. (*Rapid, Quantitative Microassay for the Monokine Respiration Inhibition Factor*, J. Immunol. Meth. 101:97-108 (1987). The permeabilized cells were suspended in respiration medium (250mM sucrose, 20mM HEPES pH 7.1, 10mM $MgCl_2$, 2mM $KH_2PO_4$, 1mM EDTA, and 1mM ADP) in a 2 ml chamber of a Model-5 oxygen electrode (Gilson Medical Electronics, Middleton, Wis.). The rate of $O_2$ consumption was measured using the indicated mitochondrial substrates and inhibitors.

2. RESULTS OBTAINED FROM EXAMINING THE SYNTHESIS AND RELEASE OF CYTOTOXIC FACTOR(S) FROM DIFFERENT CELL LINES ON THE INDUCTION OF MITOCHONDRIAL RESPIRATION INHIBITION IN EMT-6 CELLS

The macrophage-like cell lines RAW 264.7, PU5-1.8, J774A.1, P388$D_1$, and WR19M.1, all obtained from the American Type Culture Collection, were examined for synthesis and release of cytotoxic factor(s) that could induce inhibition of mitochondrial inhibition in EMT-6 cells. Following activation with IFN-γ and LPS, only RAW 264.7 and PU5-1.8 were found to produce detectable levels of this mediator as determined by the MTT assay (data not shown). Wells containing media without cells were included in order to demonstrate that the inhibition measured was not due to the activation agents since the triggering agents, IFN-γ and LPS, can act synergistically to induce mitochondrial respiration inhibition in EMT-6 cells.

A. Isolation and Characterization of a Subcloned Macrophage Cell Line (EA13.5) Derived from RAW 264.7 That Produces Increased Levels of Cytokine A clone that released significantly increased levels of the soluble mediator was isolated from the cell line RAW 264.7. Clones were obtained by plating RAW 264.7 in DME/F12, 10% FCS at limiting dilutions in 96 well plates. Media conditioned by growth of RAW264.7 was added to the wells (10%) to provide any autologous growth factors that may be released by the cells. Wells corresponding to a seeding of 1-10 cells were allowed to grow over a period of 2 to 5 weeks and then split into 4 wells each. Two of the quadruplicate wells were activated with IFN-γ and LPS and then assayed for production of the factor(s) that induce mitochondrial respiration inhibition in EMT-6 cells. The remaining two wells were reserved for subculturing clones that were to be further investigated. The procedure for the MTT assay on EMT-6 target cells was modified in the following manner to permit assay of large numbers of samples. Samples of conditioned supernatant from the two triggered wells of each of the clones were pooled and titered at dilutions of 1:3 into three successive wells of a 96 well plate containing EMT-6 target cells as described previously. After 18 hr of incubation, MTT dye was added and the reduction to MTT formazan was determined as previously described. Visual inspection of the resulting MTT formazan absorbance values and comparison to a sample of conditioned supernatant obtained from parental RAW264.7 cells was used to detect clones that demonstrated a greater inhibition of MTT reduction to MTT formazan. Clones that expressed increased cytotoxic activity were cultured from one of the two non-activated wells and the process was repeated. Finally, five clones that showed reproducible enhanced production of mitochondrial respiration inhibition activity were expanded in tissue culture plates for detailed studies. From a total of 250 clones isolated from RAW 264.7, one clone, designated EA13.5, was found to produce cytotoxic mediator at a level that was significantly greater on a per cell basis than that of RAW 264.7 and of BCG-activated peritoneal macrophages (Table I). Furthermore, when the capacity for induction of $NO_2$ synthesis in EMT-6 was measured for the EA13.5 conditioned supernatant it was found that the level of $NO_2$ induction was decreased compared to the level induced by conditioned supernatant obtained from RAW264.7 cells.

TABLE I
EFFECT OF CONDITIONED SUPERNATANT OBTAINED FROM DIFFERENT CELL SOURCES ON EMT-6 TARGET TUMOR CELLS

| | EMT-6 MR inhibition | Induction of EMT-6 nitrite synthesis | Mφ nitrite synthesis |
|---|---|---|---|
| BCG-activated Mφ | 934 | 309 | 41 |
| RAW 264.7 | 266 | 171 | 36 |
| EA13.5 | 641 | 72 | 24 |

Mitochondrial respiration (MR) inhibition was determined using the MTT assay where 1 u/ml was the amount of the dilution of 1 ml of conditioned supernatant (CS) required to yield 50% inhibition. Induction of nitrite synthesis in the EMT-6 target cell was also expressed as the dilution of CS required to reach a 50% level of the maximal nitrite synthesis generated by a standard sample of Mφ CS. Nitrite synthesis by the Mφ cell source was expressed as μM concentration of nitrite. RAW264.7 and EA13.5 cells were triggered at a density of $1 \times 10^6$ per ml. Mφ were triggered at a density of $6.6 \times 10^6$ per ml.

B. Conditions for Triggering Production of Conditioned Supernatant in EA13.5 Cells The condition for triggering production of conditioned supernatant in EA13.5 cells were as follows. EA13.5 cells were grown to a density of $0.54 \times 10^6$ per ml and triggered in EX-CELL 300 medium containing 0.2% FCS. Treatment with IFN-γ at the indicated concentrations was allowed to procede for 9 hr and then medium was replaced with fresh medium containing the indicated amounts of LPS. This data is shown in FIG. 1A.

Figure 1B:
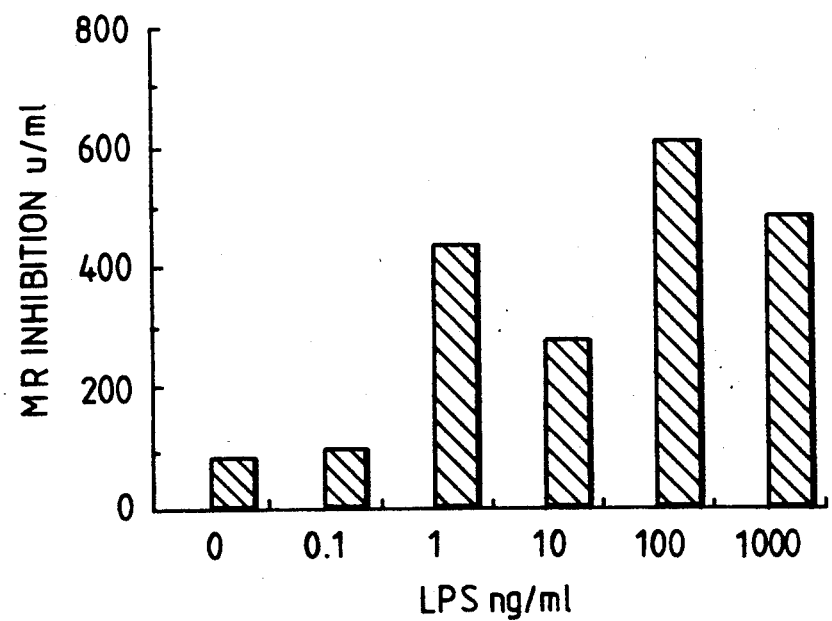
FIG. 1B demonstrates the levels of LPS that are required for triggering following 9h treatment with 20 u/ml of IFN-γ. Conditioned supernatant was harvested in all cases 16h after addition of LPS. Specific methods are set forth in Example I.

The results from FIGS. 1A and 1B demonstrate that the triggering of EA13.5 cells for release of the cytotoxic factor was found to require at least 1u/m (6 femtomolar) IFN-γ either in combination with, or followed subsequently with, at least 1.25 nanomolar LPS. When the treatment with IFN-γ preceded triggering with LPS, the EA13.5 cells were most competent for triggering with LPS for a period between 6 to 12 hr after beginning the treatment with IFN-γ.

Figure 2C:
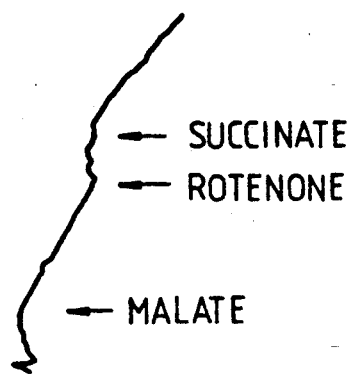
FIG. 2C) EMT-6 cells treated with a 1:10 dilution of conditioned supernatant produced by murine BCG-activated macrophages. Specific methods are set forth in Example I.
Figure 2B:
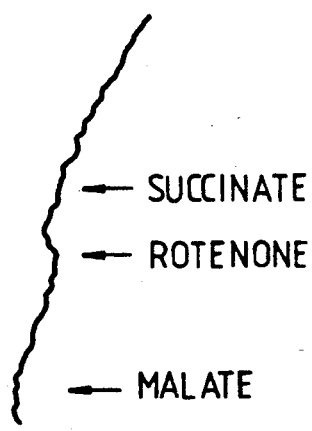
FIG. 2. $O_2$ consumption by EMT-6 cells measured on a Gilson Model-5 oxygen electrode. The $O_2$ consumption tracings are FIG. 2A) untreated EMT-6 cells, FIG. 2B) EMT-6 cells treated 18 hr with a 1:10 dilution of conditioned supernatant produced by triggered EAI13.5 cells.
Figure 2A:
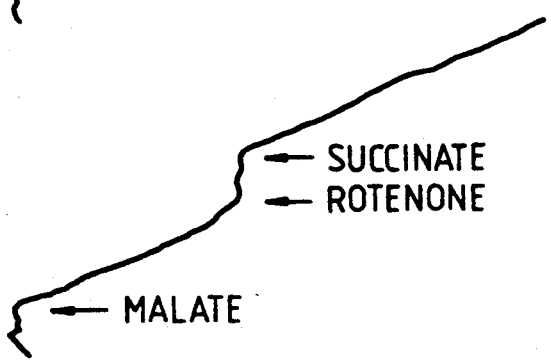

C. Confirmation of Inhibition of Mitochondrial Respiration Inhibition of EMT-6 Cells by $O_2$ Consumption Measurements The inhibition of mitochondrial respiration in EMT-6 cells was confirmed by measurement of $O_2$ uptake using a Gilson $O_2$ electrode (FIG. 2). $O_2$ consumption by EMT-6 cells measured on a Gilson Model-5 oxygen electrode. The $O_2$ consumption tracings are FIG. 2A) untreated EMT-6 cells, FIG. 2B) EMT-6 cells treated 18 hr with a 1:10 dilution of conditioned supernatant produced by triggered EA13.5 cells and; FIG. 2C) EMT-6 cells treated with a 1:10 dilution of conditioned supernatant produced by murine BCG-activated macrophages. Specific methods are set forth in Example I.

Complex I (NADH-coenzyme Q reductase) was 66% inhibited by conditioned supernatant produced by EA13.5 and Complex II (Succinate-coenzyme Q reductase) was 60 % inhibited compared to untreated EMT-6 cells. Conditioned supernatant produced by BCG-activated macrophages inhibited Complex I and II by 73% and 60% respectively.

D. Conditioned Supernatants From EAl13.5 Cells Do NOT Contain IFN-γ

ELISA assay kits were used to demonstrate that the EA13.5 conditioned supernatant contained no detectable IFN-γ. On the other hand, conditioned supernatant obtained from several preparations of BCG-activated peritoneal macrophages were found to contain IFN-γ at levels varying from 117 to 188 u/ml in the ELISA assay. Furthermore, the addition of ten-fold excess amounts of anti-IFN-γ neutralizing antibody to the EA13.5 conditioned supernatant was shown have no effect on the mitochondrial respiration inhibition activity in EMT-6 (697 u/ml in the absence of antibody vs 662 u/ml in the presence of antibody), whereas the antibody inhibited 90% of the mitochondrial respiration inhibition activity of IFN-γ titered on EMT-6 in the presence of LPS (6893 u/ml without antibody vs 653 u/ml in the presence of the antibody). Neutralizing antibody was also reported by Amber et al. (*Cytotoxic activated macrophage (CAM) conditioned medium: identification of the soluble factors inducing cytotoxicity and the L-arginine dependent effector mechanism (LADEM)* J. Leukoc. Biol. 46:307 (1989)) to neutralize 78% of the mitochondrial respiration inhibition activity of murine BCG-activated peritoneal macrophage conditioned supernatants. Anti-TNF neutralizing antiserum did not inhibit the mitochondrial respiration inhibition activity of conditioned supernatant produced by EA13.5 and a combination of anti-TNF and anti IFN-γ neutralizing antibody also did not inhibit the EA13.5 conditioned supernatant. The anti-TNF antiserum was used at a concentration ten-fold higher than the amount which 100% neutralized TNF activity contained in the conditioned supernatant as determined by the L929 cell TNF assay.

The mechanism by which MR inhibition is believed to occur has been suggested to be due to synthesis of nitric oxide which may interact with the iron-sulfur centers of complex I and II of the electron transport chain and of aconitase. However, we demonstrate in Example II that MR inhibition by macrophage conditioned supernatant may also occur by mechanisms that may be independent of the L-arginine dependent oxide nitric pathway. Comparison of macrophage conditioned supernatant versus the conditioned supernatant produced by EA13.5 showed differences in the levels of nitric oxide synthesis induced in EMT-6 cells.

EXAMPLE II

L-ARGININE INDEPENDENT TUMOR CELL MITOCHONDRIAL RESPIRATION INHIBITION ACTIVITY DISPLAYED BY A MACROPHAGE CYTOTOXIN OBTAINED FROM CONDITIONED SUPERNATANT

1. MATERIALS AND METHODS EMPLOYED

A. Materials and Reagents Used

Bacterial lipopolysaccharide (*E. coli* serotype 0128:B12 phenol extracted, LPS), and MTT dye, ADP, malate, succinate, rotenone and digitonin were obtained from Sigma Chemical Co., St. Louis, Mo. Recombinant mouse gamma interferon (rIFN-$\gamma$), neutralizing rat monoclonal antibody to IFN-$\gamma$ and the ELISA kit for mouse IFN-$\gamma$ was obtained from Amgen Biologicals, Thousand Oaks, Calif. Rat monoclonal anti-mouse IFN-$\gamma$ antibody, and mouse interferon alpha/interferon beta (IFN-$\alpha$/IFN-$\beta$) were purchased from Lee Biomolecular Research, San Diego, Calif. Recombinant murine TNF (tumor necrosis factor) and IL-1, and antibody to TNF were obtained from Genzyme Corp., Boston, Mass.

Endotoxin screened fetal calf serum (FCS), powdered DME/F12 media, and EX-CELL 300 media were obtained from Hazelton Research Products, Lenexa, Kans. Penicillin/streptomycin (P/S) was obtained from GIBCO Laboratories, Grand Island, N.Y. The media used in this study were determined to contain less than 0.5 ng/ml lipopolysaccharide (LPS) based on a Limulus amebocyte lysate (LAL) test by Associates of Cape Cod, Woods Hole, Mass. Bacillus Calmette-Guérin (BCG) was obtained from Bionetics (Chicago, Ill.), or Antigen Supply House, Chatsworth, Calif.

EMT-6, a murine mammary adenocarcinoma was supplied by Dr. R. Kallman, Stanford University. RAW 264.7 and L929 cells were obtained from American Type Culture Collection, Rockville, Md. Target cells were maintained in DME/F12 containing 5 percent FCS. Peritoneal macrophages were obtained in a manner as generally described in Kilbourn, R. G., et al., with some modifications (*Activated Macrophages Secrete a Soluble Factor That Inhibits Mitochondrial Respiration of Tumor Cells*, J. Immunol. 133:2577–2581 (1984)).

B. Producing Peritoneal Macrophages and Conditioned Supernatants From the Peritoneal Macrophages and RAW 264.7

1. Conditioned Supernatants From the Peritoneal Macrophages

Eight to twelve week old CD-1 Swiss male mice (obtained from Harlan Sprague Daley, Inc., Indianapolis, Ind.) were injected intraperitoneally with $1 \times 10^7$ colony forming units of BCG on day zero. A booster injection of $1 \times 10^7$ colony forming units was given on approximately day 21 and the macrophages were harvested by peritoneal lavage on day 25.

Peritoneal exudate cells were centrifuged and resuspended in DME/F12 containing 10 mM HEPES buffer pH 7.4 and Penicillin-Streptomycin. Cells were allowed to adhere to tissue culture plates for 2 hours at a density of $3.6 \times 10^6$ cells/cm$^2$ surface area. Non-adherent cells were removed by rinsing the plates gently with PBS three times and additional DME/F12/HEPES/P/S media (0.54ml/cm$^2$) was added to the plates. The adherent cells were estimated to be 85–95 percent macrophages by Wright-Giemsa stain. The adherent peritoneal macrophage cultures were triggered by adding LPS (112 nanomolar). Conditioned supernatant (CS) was collected 18 hours after LPS addition.

2. Conditioned Supernatants From RAW 264.7

RAW264.7 is maintained in either DME/F12 containing 5 to 10% FCS or in EX-CELL 300 medium containing 0.2% FCS and 10 to 25mM HEPES, pH 7.4. Media previously conditioned by growth of RAW264.7 was added (10%) to the media to provide any autologous growth factors that may be released by the cells. This macrophage cell line is able to grow adherent to tissue culture dishes to a maximum density in these media of approximately $1 \times 10^6$ cells per ml. For purposes of producing conditioned supernatant in a low protein containing medium, the cells were grown in EX-CELL 300 containing 0.2% FCS. When the macrophage cell line reached a density of $0.5 \times 10^6$ cells/ ml or higher, production of the conditioned supernatant was triggered by activation of the macrophages with IFN-$\gamma$ (20u/ml). Following a period of 6 to 12 hours of IFN-$\gamma$ treatment, the cells were triggered with LPS (12.5 nanomolar). In order to produce the conditioned supernatant in a low protein containing medium, the medium was changed by centrifugation of the cells after treatment with IFN-$\gamma$ and replacement of the cells in fresh medium containing LPS. This low protein containing medium may consist of EX-CELL 300 containing 0.2–0.05% FCS. The conditioned supernatant was collected approximately 18 hr after triggering with LPS.

C. DEAE-Sephacel Fractionation of Conditioned Supernatant

The fractionation was carried out at 4° C. 500 milliliters of conditioned supernatant were concentrated by employing a stirred-cell apparatus fitted with a YM-10 filter, obtained from Amicon Corp., Danvers, Mass., and equilibrated with 20 mM Tris.HCl pH 8.0 buffer, and then applied at a flow rate of 1 ml/min. to a $2.5 \times 8$ cm DEAE-sephacel column equilibrated in the same buffer. Unbound proteins were eluted by washing with two volumes of start buffer, and the bound proteins were eluted with a linear gradient of NaCl from 0–0.25M in the same buffer. Thirteen milliliter fractions were collected and analyzed for mitochondrial respiration inhibition and nitrite production on EMT-6 or L929 cells.

D. Determining Mitochondrial Respiration Using a 3-[4,5-dimethylthiazol-2-1]-2, 5-diphenyltetrazolium bromide (MTT) Assay Mitochondrial respiration was determined using the 3-[4,5-dimethylthiazol-2-1]-2, 5-diphenyltetrazolium bromide (MTT) assay performed generally as described in Klostergaard et al., with minor modifications (*Rapid, Quantitative Microassay for the Monokine Respiration Inhibition Factor*, J. Immunol. Meth. 101:97–108 (1987)).

EMT-6 target cells ($8 \times 10^3$/100 $\mu$l) were cultured in DME/F12 medium containing 5% fetal calf serum, penicillin and streptomycin in 96-well plates. Following overnight incubation, 50 $\mu$l of test samples (in triplicate) were added to the first well of the target plate and titered such that successive wells corresponded to a 1:3 dilution. After 18 hours more of incubation, 10 $\mu$l of 5 mg/ml MTT (Sigma Chemicals) were added to each well. Reduction of MTT to MTT formazan was allowed to continue for 60 minutes at 37° C. after which the plates were inverted and blotted dry. MTT formazan was resolubilized by the addition of 100 μl of dimethyl sulfoxide (DMSO). Absorbance was read at 570 nm in a plate reader (Molecular Devices Corp., Menlo Park, Calif.).

The value of mitochondrial respiration inhibition when applicable was expressed in units per ml, and was obtained by calculating the amount of the dilution of one ml of the test substance that caused 50 percent of the maximum inhibition of formazan production, where the minimum level of formazan production was measured for untreated control target cells and the maximum level of formazan production was measured using target cells treated with undiluted conditioned supernatant.

E. Determining Nitrite Production by Tumor Cells

The production of nitric oxide by tumor cells was determined using a colorimetric assay for nitrite. To determine the nitrite concentration in the same wells used for the mitochondrial respiration assay, 50 μl of the target cell media were removed at the termination of the 18 hours of incubation prior to MTT addition and dispensed into a secondary plate. The original plate was used in the mitochondrial respiration assay with the addition of 60 μl of fresh media containing MTT to yield a final concentration of 0.5 mg/ml. The concentration of nitrite in the media was determined on the secondary plate by addition of 50 μl of Greiss reagent (1% sulfanilamide/0.1% naphthyl-ethylenediamine dihydrochloride/2.5% phosphoric acid) and measurement of the absorbance at 540 nm.

For nitrite production by target cells, the value in units per ml was obtained by calculating the dilution from one ml of the test sample that induced the target cells to produce 50 percent of the maximal amount of nitrite. The maximum amount of nitrite produced was determined by treatment of EMT-6 cells with undiluted conditioned supernatant, while the minimum or background was the value for untreated cells.

The concentration of endogenous nitrite present in conditioned supernatant or in media of treated EMT-6 cells was determined by addition of an equal volume of Greiss reagent to 50 μl of test supernatant. A standard curve for quantitation of nitrite was constructed using dilutions of a stock sodium nitrite solution.

F. Tumor Necrosis Factor Bioassay

Many in vitro studies have demonstrated that macrophages can selectively destroy tumor cells. This phenomenon is a nonphagocytic, antibody-independent process. Although the mechanism for this reaction is not clear, several products secreted by macrophages have been identified that possibly play a role in this process. One of these products is tumor necrosis factor.

TNF was determined by using a cytolytic assay with L929 cells as targets as shown in Klostergaard (A Rapid Extremely Sensitive, Quantitative Microassay for Cytotoxic Cytokines, Lymphokine Res. 4:309-318 (1985). L929 cells were seeded at $1.5 \times 10^4$ per well in a 96 well flat bottom plate and incubated overnight. Following addition of actinomycin D (1.0 μg/ml), the test substance was added to the first well and titered at dilutions of 1:3. After 18 hours of incubation, neutral red was added to each well at a final concentration of 0.002%. Following an additional 2 hours of incubation, the plates were washed with PBS and the bound dye was resolubilized with 70% ethanol and 0.6% glacial acetic acid. The absorbance was read at 540 nm in the plate reader.

The value for TNF activity in units per ml was obtained by calculating the amount of the dilution from one ml that yielded 50 percent lysis of the L929 monolayer, where the minimal cytolysis was measured for untreated targets and the maximal cytolysis was measured using targets treated with a standard preparation of TNF which induced greater than 99% lysis of the monolayer.

G. Correlation Between Anti-Viral Activity and Mitochondrial Respiration Inhibition Mediated by rIFN-γ

In experiments designed to quantitate the possible contribution of rIFN-γ/LPS in macrophage conditioned supernatant to mitochondrial respiration inhibition of EMT-6 cells, 1 unit of anti-viral activity of rIFN-γ when assayed in the presence of LPS, was found to correspond to 2 to 3 mitochondrial respiration inhibition units. This equivalence basis was employed in all subsequent rIFN-γ antibody neutralization experiments.

2. COMPARISON OF RESULTS OBTAINED FROM EXAMINING THE EFFECTS OF IFN-γ AND CONDITIONED SUPERNATANT ON THE MITOCHONDRIAL RESPIRATION OF EMT-6 CELLS

Figure 3A:
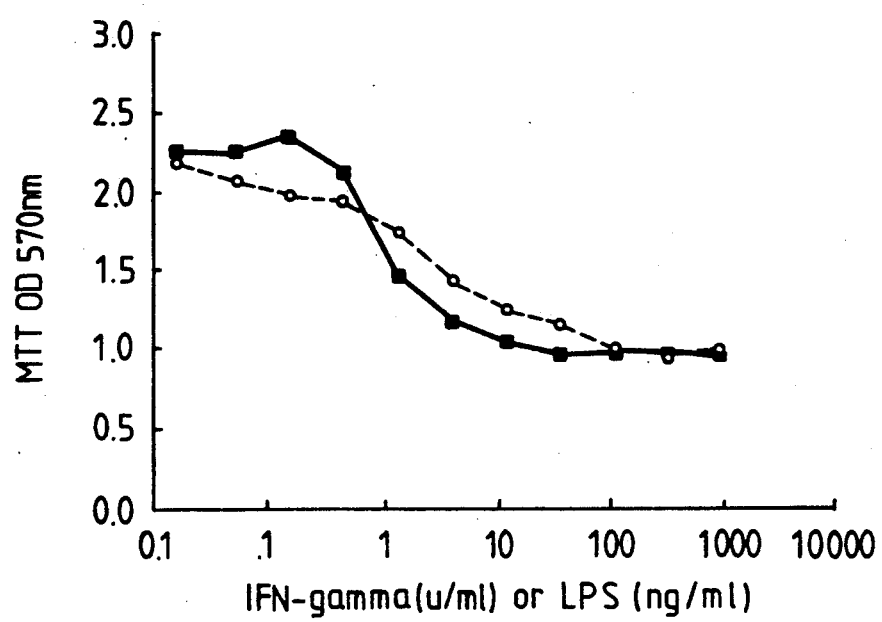
FIG. 3A.
Figure 3B:
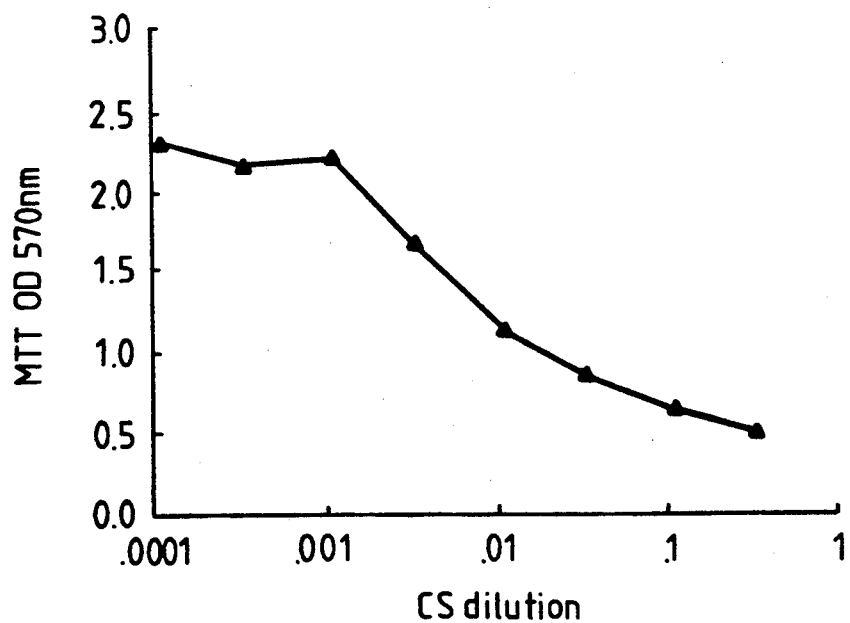
FIG. 3B.

FIGS. 3A and 3B compare the mitochondrial respiration inhibition of IFN-γ and conditioned supernatant.

FIG. 3A demonstrates the effect of LPS (o) concentration on inhibition of mitochondrial respiration mediated by rIFN-γ, as well as the dose response for inhibition of mitochondrial respiration with rIFN-γ (■) in the presence of an excess of LPS (25 nanomolar).

The effects of the combination of rIFN-γ and LPS on the mitochondrial respiration of EMT-6 cells were examined (FIG. 3A). When a constant amount (1,000 antiviral units/ml) of rIFN-γ was maintained and the concentration of LPS was varied, a minimum of 12.5 nanomolar of LPS was required to produce the maximal inhibition of mitochondrial respiration (FIG. 3A).

When the concentration of LPS was kept constant (25 nanomolar), a minimum of 30 antiviral units/ml IFN-γ was required to produce maximal inhibition of mitochondrial respiration. Since macrophage conditioned supernatant contained a considerable amount of LPS and considering the possibility that it could contain some IFN-γ from contaminating lymphocytes in the macrophage preparation, combined rIFN-γ/LPS were compared with conditioned supernatant for their ability to inhibit mitochondrial respiration.

FIG. 3B shows the dose-dependent inhibition of mitochondrial respiration for EMT-6 treated with conditioned supernatant ( ). The $OD_{570}$ of MTT formazan obtained for mitochondrial respiration inhibition assays with EMT-6 cells are shown for comparison of the effect of conditioned supernatant and IFN-γ.

EMT-6 mitochondrial respiration was expressed in FIGS. 3A and 3B as $OD_{570}$ of MTT formazan dye in order to demonstrate that conditioned supernatant is indeed more potent in inhibiting respiration than IFN-γ.

Treatment of EMT-6 cells with conditioned supernatant or combined rIFN-γ/LPS resulted in a dose-dependent mitochondrial respiration inhibition. As shown in FIG. 3B, the maximal inhibition of mitochondrial respiration (depicted by the lower $OD_{570}$) observed for conditioned supernatant (O.D.~0.5) was consistently and substantially greater than the maximal inhibition achieved with combined rIFN-γ/LPS (O.D.~1.0) as seen in FIG. 3A.

The effects of conditioned supernatant and rIFN-γ in combination with LPS or cytokines on mitochondrial respiration in EMT-6 cells was studied (Table II). Mitochondrial respiration inhibition is expressed as a percentage to facilitate comparison of the various treatments. The mitochondrial respiration by EMT-6 cells was once again inhibited to a much higher degree by crude conditioned supernatant (84%) than by rIFN-γ in combination with LPS or other cytokines (19-41%). Treatment of the target cells with ten-fold higher doses of rIFN-γ showed no additional inhibition (FIG. 3A).

TABLE II

EFFECTS OF CONDITIONED SUPERNATANT AND CYTOKINES ON EMT-6 MITOCHONDRIAL RESPIRATION

| Test Sample (a) | Percent Inhibition of MR (b) |
|---|---|
| CS | 84 |
| IFN-γ | 21 |
| IFN-γ + LPS | 40 |
| IFN-γ + TNF | 38 |
| IFN-γ + IL1 | 39 |
| IFN-γ + TNF + IL1 + LPS | 41 |
| TNF + IL1 | 4 |
| IFN-α/IFN-β + IFN-γ | 19 |

(a) The dose of samples are: conditioned supernatant 1:3 dilution, IFN-γ 1250 u/ml, LPS 1000 ng/ml, TNF 10 u/ml, IL1 10 u/ml, IFN-α/IFN-β 2000 u/ml.
(b) For purposes of comparison of the response of EMT-6 cells to treatment with conditioned supernatant versus combinations of cytokines, the percent inhibition of mitochondrial respiration was expressed as $[1-OD_{test\ sample} / OD_{untreated})] \times 100$.

3. COMPARISON OF MOLECULAR SIZE DETERMINATION BY GEL FILTRATION OF CONDITIONED SUPERNATANT FROM EA13.5 MACROPHAGE CELLS AND OF CONDITIONED SUPERNATANT FROM PERITONEAL MACROPHAGES

Figure 4A:
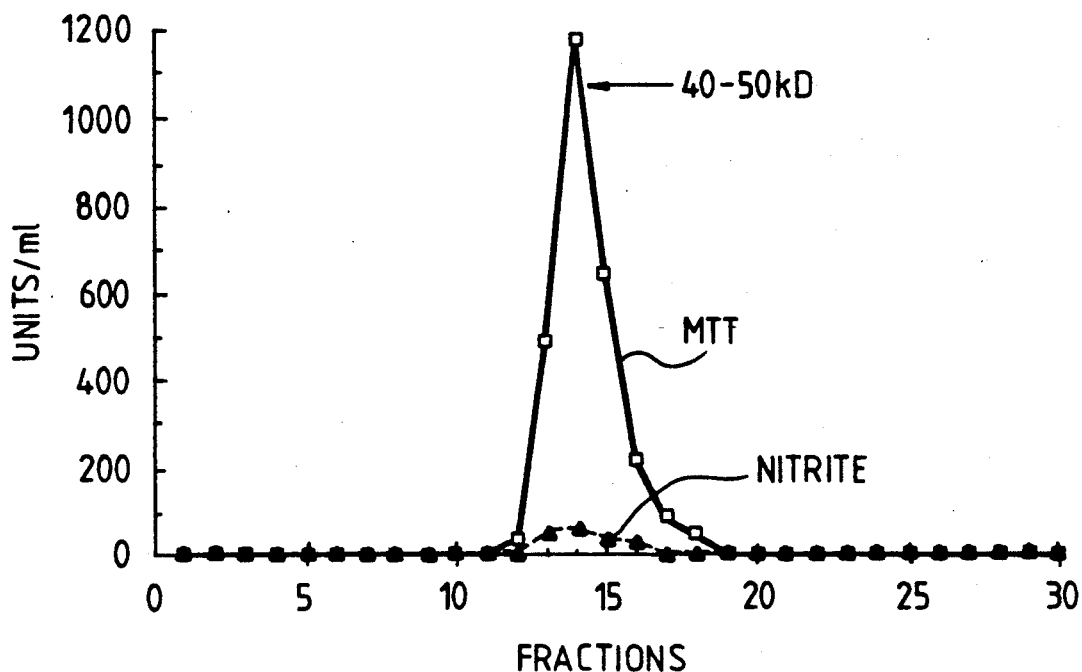
FIG. 4A.

FIG. 4A presents the molecular size determination by gel filtration of conditioned supernatant from EA13.5 macrophage cell line by studying both mitochondrial respiration inhibition, as well as nitrite production. The results demonstrate that the NO-independent cytotoxin elutes as a 40-50 kd protein and has negligible NO induction activity.

Figure 4B:
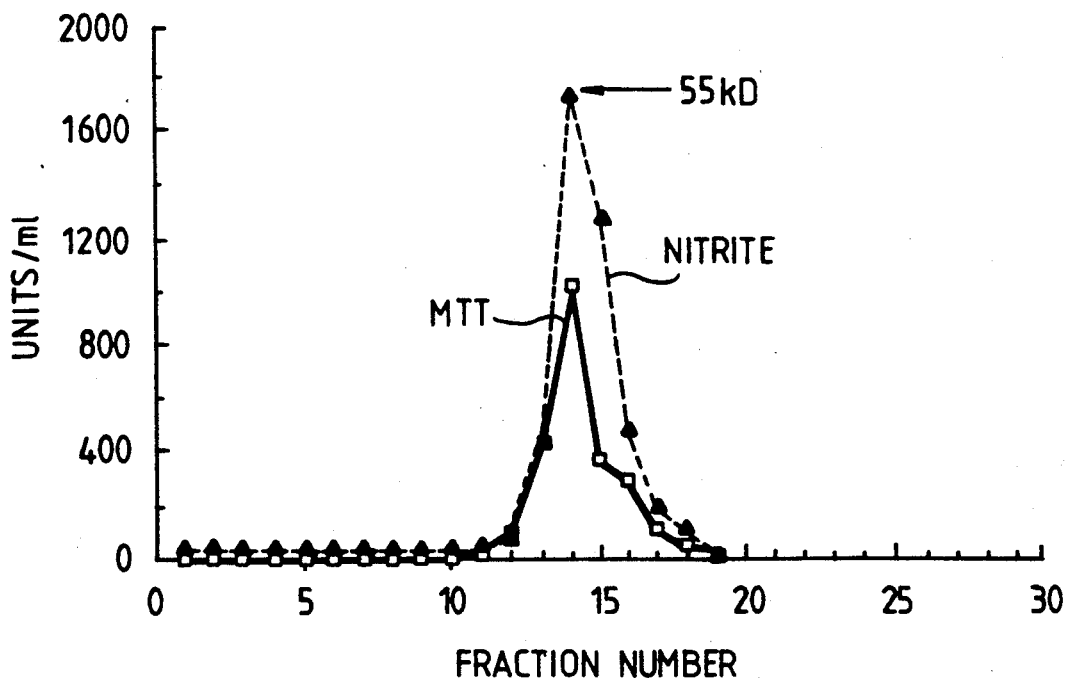
FIG. 4B.

FIG. 4B presents the molecular size determination by gel filtration of conditioned supernatant from peritoneal macrophages by studying both mitochondrial respiration inhibition, as well as nitrite production. The results demonstrate that both NO induction activity and MRI co-elutes, but NO induction activity is the major component.

4. TESTING CONDITIONED SUPERNATANT FOR PRESENCE OF IFN-γ BY DEAE-5PW

FIG. 5A shows the effect conditioned supernatant-/DEAE-fractions has on mitochondrial respiration inhibition, nitrite production and the distribution of IFN-γ. FIG. 5A demonstrated that greater than 90 percent of the total IFN-γ present in the conditioned supernatant did NOT coincide with mitochondrial respiration inhibition. Thus, 90% of the observed mitochondrial respiration inhibition, found in the conditioned supernatant, was independent of IFN-γ activity.

Therefore, this data clearly indicates that IFN-γ does not participate in either the cytotoxic process or the mitochondrial respiration inhibition found in the conditioned supernatant disclosed in the instant invention.

5. DEAE-SEPHACEL FRACTIONATION OF CONDITIONED SUPERNATANT

Since the macrophage conditioned supernatant contained a significant amount of TNF activity, the conditioned supernatant was subjected to DEAE-Sephacel fractionation in order to separate the TNF activity from other cytotoxic activities.

FIG. 5B shows the profile for a sample of conditioned supernatant (500 ml) fractionated on a (2.5cm×8cm) DEAE-Sephacel column. Conditioned supernatant was concentrated and equilibrated in 20 mM Tris.HCl pH 8.0 and applied to the 1×10 cm DEAE-Sephacel column equilibrated in start buffer. Fractions (13ml) were assayed for mitochondrial respiration inhibition (□) and nitrite production (Δ) using EMT-6 cells and for TNF activity using L-929 cells. The TNF activity as demonstrated with L-929 cells, elutes between fractions 38-42 in greater than 0.2 MNaCl.

Under the elution conditions used, TNF activity was well resolved from those of mitochondrial respiration inhibition (FIG. 5B).

6. ENHANCED PRODUCTION OF L-ARGININE INDEPENDENT MACROPHAGE CYTOTOXIN IN SELECTED MEDIA

Conditioned supernatant was collected from macrophages triggered with LPS in various selected media. The media were obtained commercially. The concentration of L-arginine was 700 μM for DME/F12 and 1575. Support for this arginine concentration correction is found on page 31, Table III. μM for EXCEL medium. MEM was reconstituted at the concentrations shown.

The results from Table III demonstrates:
(1) LPS was required for induction of the cytotoxic factor.
(2) L-arginine analogue MMA ($N^G$-monomethyl-L-arginine) increased production of the factor.
(3) Low concentrations of L-arginine (<100 μM) caused reduced production of the factor initially after LPS triggering (0-6 hours) but still resulted in significant production of cytotoxic factor by 18 hr (indeed higher levels of factor than in DME/F12).
(4) EX-CELL 300 media (J. R. Scientific, Woodland, Calif.) yielded significantly higher levels of factor than the DME/F12 media.

TABLE III

PRODUCTION OF L-ARGININE INDEPENDENT MACROPHAGE CYTOTOXIN IN SELECTED MEDIA AS DETERMINED BY MITOCHONDRIAL RESPIRATION INHIBITION
Mitochondrial Respiration Inhibition of EMT-6 Cells (units/ml)

| | | | |
|---|---|---|---|
| DME/F12 | 0-18 hr | | |
| −LPS | 152 | | |
| +LPS | 6645 | | |
| +LPS + MMA | 11493 | | |
| DME/F12 | 0-5 hr | 5-18 hr | 18-25 hr |
| +LPS | 5770 | 5030 | 732 |
| MEM | 0-6 hr | 6-18 hr | |
| 0 μM Arg | 4252 | 45991 | |

TABLE III-continued

PRODUCTION OF L-ARGININE
INDEPENDENT MACROPHAGE CYTOTOXIN
IN SELECTED MEDIA AS DETERMINED BY
MITOCHONDRIAL RESPIRATION INHIBITION
Mitochondrial Respiration Inhibition of EMT-6 Cells
(units/ml)

| | | |
|---|---|---|
| 20 | 5819 | 54622 |
| 50 | 5570 | 38535 |
| 100 | 16136 | 4165 |
| 500 | 33682 | 21870 |
| 1000 | 25726 | 36811 |
| EX-CELL 300 | 0–6 hr | 6–18 hr |
| 1575 μm Arg | 27760 | 2144 |
| 0 Arg | 35585 | 5528 |

7. CHARACTERIZING THE MACROPHAGE CYTOTOXIN AS A WEAKLY ACIDIC GLYCOPROTEIN

The macrophage cytotoxin described in this invention is weakly acidic (as determined by DEAE-5PW (diethylaminoethyl) because the MR inhibition activity was eluted at very low ionic strength) and a glycoprotein (as determined by binding to lentil lectin) (see FIG. 5A).

A. Lentil Lectin Sepharose Chromatography

The ability to bind to lentil lectin sepharose column was used to determine that the macrophage cytotoxin was a glycoprotein. Briefly, concentrated conditioned supernatant (equilibrated with Dulbecco's-phosphate buffered saline, pH 8.0 containing 0.2 mM calcium chloride) was applied to a lentil lectin sepharose (LLS, 10×2.5 cm) column. The flow-through was collected and the column was washed with the above buffer. The bound proteins were eluted with five-column volumes of alpha-methyl mannoside in the same buffer. The eluted fractions were tested for mitochondrial respiration inhibition and nitrite production.

The results indicated that while both mitochondrial respiration inhibition and nitrite inducing protein components are found in the conditioned supernatant, only the mitochondrial respiration inhibition protein bound (100%) and eluted from the LLS column quantitatively (65% recovered), while <7% of the nitrite production component eluted from the same column. Thus, the presence of the mitochondrial respiration inhibition protein was independent of the nitric oxide pathway since these were biochemically dissociable.

Thus, from this study, the inventors concluded that the macrophage cytotoxin described in this invention is a glycoprotein.

B. Isoelectric Focusing

To determine if the macrophage cytotoxin was an acid or basic protein, isoelectric focusing using rotofor was employed.

Approximately 50 ml of concentrated conditioned supernatant (containing about 1 mg of total protein) was subjected to isoelectric focusing in the rotofor apparatus (BioRad Co, Ca.). Ampholytes were employed at a final concentration of 1% and in a pH range of 3.5 to 10. Primary electrofocusing was performed for 6 hr (according to manufacturer's protocol) followed by refocusing of the fractions in the pI range of 6.5–8.5 for an additional 12 hr. Fractions obtained were subjected to the MTT assay and nitrite assay as described above.

The results from preliminary isoelectric focusing experiments demonstrated that the mitochondrial respiration inhibition activity focuses with a pI of about 7.5–8.0.

Thus, from experiments of this type, the inventors have concluded that the macrophage cytotoxin is a weakly acidic glycoprotein.

8. CONCLUSION

Macrophage conditioned supernatant mediated cytotoxicity may proceed via a mitochondrial respiration inhibition pathway that is independent of L-arginine derived nitric oxide. This was demonstrated by 1) conditioned supernatant which can be produced from a newly established macrophage cell line (EA13.5) that produces enhanced cytotoxicity via a mechanism that is independent of L-arginine derived nitric oxide, and 2) characterization of this cytotoxin from murine peritoneal macrophage conditioned supernatants.

Furthermore, these processes appear to be independent of any contaminating IFN-γ and TNF in these supernatants. These macrophage derived factor(s) are indeed distinct from and more potent in their bioactivities than IFN-γ in combination with LPS, TNF, and interleukin-1.

Although other theories or mechanisms were not addressed, they should be considered as within the realm of possibility and the described mechanism is not intended to be limiting the invention. Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced as defined by the claims.

What is claimed is:

1. An isolated macrophage cytotoxin produced by:
   a) culturing macrophage cell line RAW 264.7 having ATCC accession number TIB 71 in EX-CELL 300 medium;
   b) adding IFN-γ to the medium in a concentration ranging from about 1 unit/ml to about 100 units/ml;
   c) exchanging the medium containing IFN-γ with fresh medium containing lipopolysaccharide in a concentration ranging from about 1.25 nanomolar to about 125 nanomolar, such that no detectable levels of IFN-γ remain;
   d) separating the cultured macrophages from the supernatant at least 6 hours after the addition of medium containing lipopolysaccharide;
   e) collecting the supernatant; and
   f) isolating the macrophage cytotoxin from the supernatant, wherein said macrophage cytotoxin:
      i) is a glycoprotein (as determined by binding to lentil lectin sepharose) having a molecular weight of between about 40 kD and about 50 kD as measured by gel filtration and binds to DEAE-5PW or DEAE-sephacel;
      ii) inhibits of in vitro mitochondrial respiration independent of nitric oxide production;
      iii) has cytotoxic activity independent of the presence of IFN-γ; and
      iv) causes in vitro cytostasis.

2. An isolated macrophage cytotoxin produced by:

a) culturing macrophage cell line EA13.5 having ATCC accession number CRL 10934 in EX-CELL 300 medium;
b) adding IFN-γ to the medium in a concentration ranging from about 1 unit/ml to about 100 units/ml;
c) exchanging the medium containing IFN-γ with fresh medium containing lipopolysaccharide in a concentration ranging from about 1.25 nanomolar to about 125 nanomolar, such that no detectable levels of IFN-γ remain;
d) separating the cultured macrophages from the supernatant at least 6 hours after the addition of medium containing lipopolysaccharide;
e) collecting the supernatant; and
f) isolating the macrophage cytotoxin from the supernatant, wherein said macrophage cytotoxin:
  i) is a glycoprotein (as determined by binding to lentil lectin sepharose) having a molecular weight of between about 40 kD and about 50 kD as measured by gel filtration and binds to DEAE-5PW or DEAE-sephacel;
  ii) inhibits of in vitro mitochondrial respiration independent of nitric oxide production;
  iii) has cytotoxic activity independent of the presence of IFN-γ; and
  iv) causes in vitro cytostasis.

3. The cytotoxin in claim 1, wherein, in addition to lipopolysaccharide, $N^G$-monomethyl-L-arginine (MMA) is added in a concentration ranging from about 100 μM to about 500 μM.

4. The cytotoxin of claim 2, wherein, in addition to lipopolysaccharide, $N^G$-monomethyl-L-arginine (MMA) is added in a concentration ranging from about 100 μM to about 500 μM.

5. The macrophage cytotoxin of claim 1, wherein said cytotoxin is isolated by a series of protein fractionation steps including lentil lectin sepharose chromatography, DEAE-sephacel or DEAE-5PW chromatography, and gel filtration.

6. The macrophage cytotoxin of claim 2, wherein said cytotoxin is isolated by a series of protein fractionation steps including lentil lectin sepharose chromatography, DEAE-sephacel or DEAE-5PW chromatography, and gel filtration.

* * * * *

UNITED STATES PATENT AND TRADEMARK OFFICE
CERTIFICATE OF CORRECTION

PATENT NO. : 5,198,428

DATED : March 30, 1993

INVENTOR(S) : Mathoor Sivaramakrishnan, Stanley D. Tucker, Jim Klostergaard and Gabriel Lopez-Berestein It is certified that error appears in the above-indentified patent and that said Letters Patent is hereby corrected as shown below:

Column 4, line 26, delete "EAI13.5" and replace with --EA 13.5 --.

Column 6, line 26, delete "EAI13.5" and replace with --EA 13.5 --.

Column 6, line 38, delete "(2ou/ml)." and replace with --(20u/ml).--.
Column 9, line 52, delete "0.54x106" and replace with --$0.54 \times 10^6$--.
Column 10, line 24, delete "EAI13.5" and replace with --EA 13.5 --.
Column 12, line 13, delete "(i0%)"and replace with --(10%) --.
Column 14, line 59, delete "()" should read -- (▲) --.

Signed and Sealed this

First Day of March, 1994

Attest:

BRUCE LEHMAN

Attesting Officer

Commissioner of Patents and Trademarks